(12) United States Patent
Weisman et al.

(10) Patent No.: US 6,734,195 B2
(45) Date of Patent: May 11, 2004

(54) PHARMACEUTICAL COMPOSITIONS CONTAINING DONEPEZIL HYDROCHLORIDE

(75) Inventors: Alexander Weisman, Kiryat Ekron (IL); Chalil Abu Gnim, Laqia (IL); Rina Uzan, Beer-Sheva (IL); Joseph Kaspi, Givatayim (IL)

(73) Assignee: Chemagis Ltd., Tel Aviv (IL)

( * ) Notice: Subject to any disclaimer, the term of this patent is extended or adjusted under 35 U.S.C. 154(b) by 8 days.

(21) Appl. No.: 10/208,791

(22) Filed: Aug. 1, 2002

(65) Prior Publication Data

US 2004/0002517 A1 Jan. 1, 2004

(30) Foreign Application Priority Data

Jul. 1, 2002 (IL) .................................. 150509

(51) Int. Cl.[7] ..................... A61K 31/445; C07D 211/10
(52) U.S. Cl. ....................... 514/315; 546/206
(58) Field of Search ................. 514/212, 357; 546/206

(56) References Cited

U.S. PATENT DOCUMENTS

| 4,895,841 A | * | 1/1990 | Sugimoto et al. ........... 514/212 |
| 5,985,864 A | | 11/1999 | Imai et al. |
| 6,140,321 A | | 10/2000 | Imai et al. |

OTHER PUBLICATIONS

RN #120011–70–3, File Registry, Donepezil Hydrochloride.*

* cited by examiner

Primary Examiner—Alan L. Rotman
Assistant Examiner—Janet L Coppins
(74) Attorney, Agent, or Firm—Banner & Witcoff, Ltd.

(57) ABSTRACT

The invention provides a pharmaceutical composition for the treatment of dementia or Alzheimer's disease in which the active therapeutical agent is donepezil hydrochloride in an amorphous state.

4 Claims, 3 Drawing Sheets

PHARMACEUTICAL COMPOSITIONS CONTAINING DONEPEZIL HYDROCHLORIDE

The present invention relates to stable, amorphous, donepezil hydrochloride and to pharmaceutical compositions containing it.

Donepezil hydrochloride was found as an efficient drug for the treatment of dementia and Alzheimer's disease. Its cholinergic enhancement property is considered to be the reason for the alleviation of symptoms in patients. The drug, formulated as 5 and 10 mg film coated tablets is given once daily to the patients.

The crystalline state of the active ingredient in a solid state pharmaceutical preparation may play a significant role in the behavior of the drug, once taken orally, and may influence its therapeutic effect. The crystalline state may modify the dissolution and thus influence absorption and the therapeutic effect of the drug.

Donepezil hydrochloride shows polymorphism. U.S. Pat Nos. 5,985,864 and 6,140,321 describe no less than five different crystalline forms of donepezil hydrochloride (including hydrates). In such a case it is very important that the formulation of donepezil hydrochloride will contain the same crystalline form in order to ensure the same therapeutical activity of the drug on the patients.

This, however, is not a simple goal to achieve. Reading the examples. presented in U.S. Pat. No. 5,985,864 and U.S. Pat. No. 6,140,321 one learns that the same procedures are liable to give different crystalline forms of donepezil hydrochloride. These patents claim that aging the reaction suspension prior to filtration for a specific time can control the type of crystalline form obtained. However, the same documents contain phrases cautioning the reader that these times can vary, and one cannot be sure which crystalline form will result from the crystallization process.

One way to alleviate the problem and to obtain a reproducible solid form of donepezil is to use the non-crystalline form of donepezil hydrochloride. On the one hand the problem of having a variety of crystalline forms does not exist, while on the other hand, non-crystalline amorphous solids are known to have a better solubility. As a result one can expect a good, consistent availability of the active ingredient.

Amorphous donepezil hydrochloride is mentioned in U.S. Pat. No. 5,985,864 and U.S. Pat No. 6,140,321. However, it is claimed that this form is chemically unstable and develops impurities on standing. Thus, it is described that at 40° C. the content of the impurities of crystalline donepezil hydrochloride (forms I to IV) did not change during a 12 week period, whereas the impurity content in amorphous donepezil hydrochloride changed from an initial value of 0.1% to 0.2% after 4 weeks and to 0.4% after 12 weeks. At higher temperatures even more extensive decomposition was reported. Therefore, these patents recommend the use of crystalline forms of donepezil hydrochloride only.

It has now been surprisingly found that amorphous donepezil hydrochloride is stable for an extended period of time. Thus, there was no change in the impurity content of the amorphous material stored at 40° C. After 3 and 6 months storage at 40° C. at 75% relative humidity, the highest impurity level was 0.1% with a total impurities level of 0.4%. These levels were exactly the initial values. There was no indication of a chemical degradation of amorphous donepezil hydrochloride produced according to the present invention. An aqueous solution of donepezil hydrochloride was lyophilized and a solid amorphous material was obtained.

Thus, it has now been surprisingly found that wet granulation of donepezil, hydrochloride yields, after drying and milling, a stable granulate that uniformly contains donepezil hydrochloride amorphous. This was shown by X-ray diffraction study.

Thus, there is now provided according to the present invention a pharmaceutical composition for the treatment of dementia or Alzheimer's disease in which the active therapeutical agent is donepezil hydrochloride in an amorphous state.

In preferred embodiments of the present invention there are provided pharmaceutical compositions as defined in which the amount of donepezil hydrochloride amorphous is between 1 to 30 mg.

The present invention also provides stable donepezil hydrochloride amorphous.

Testing the tablets by X-ray diffraction in order to evaluate the crystalline properties of the active material is not a simple task. Most of the donepezil tablet is inactive ingredients. Being crystalline compounds they do have X-ray diffraction pattern. This pattern has to be subtracted from the total pattern in order to see the peaks that originate from donepezil hydrochloride. The fact that donepezil hydrochloride itself is only a small part of the formulation makes it even harder. We managed to get more meaningful results measuring the X-ray diffraction of 30 mg tablets, and using a peak enhancement technique.

Figure 1:
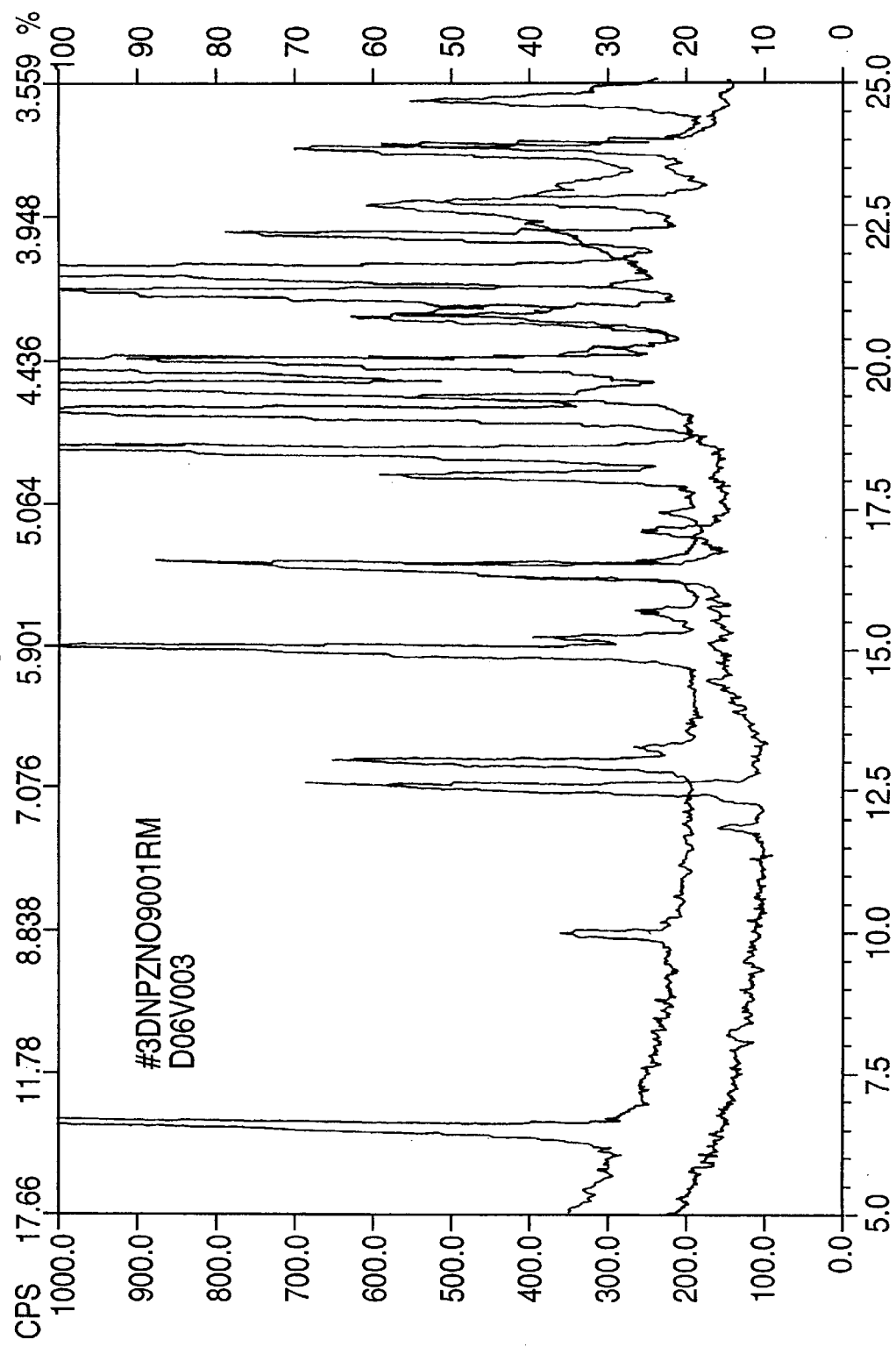
FIG. 1 is the X-ray diffraction pattern of donepezil hydrochloride having crystalline form I (top trace) and of a placebo (bottom trace). The placebo tablets were prepared from the same ingredients used to prepare our tablets and commercial Aricept® (donepezil hydrochloride) tablets.
Figure 2:
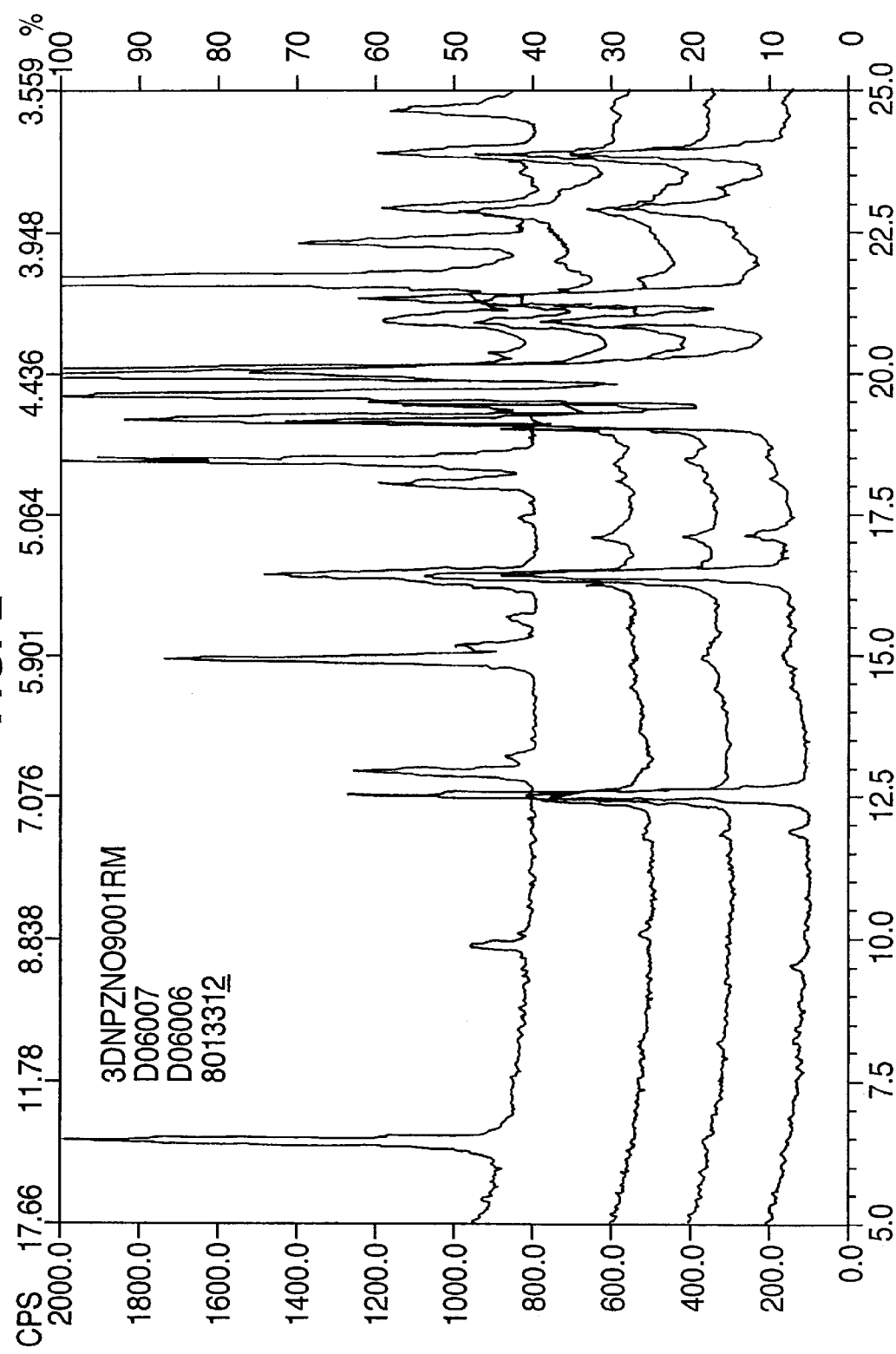
FIG. 2 is the X-ray diffraction pattern obtained from (top to bottom) donepezil hydrochloride, donepezil hydrochloride tablets prepared by wet granulation, 30 mg), donepezil hydrochloride tablets prepared by dry granulation (30 mg) and. Aricept® tablets.
Figure 3:
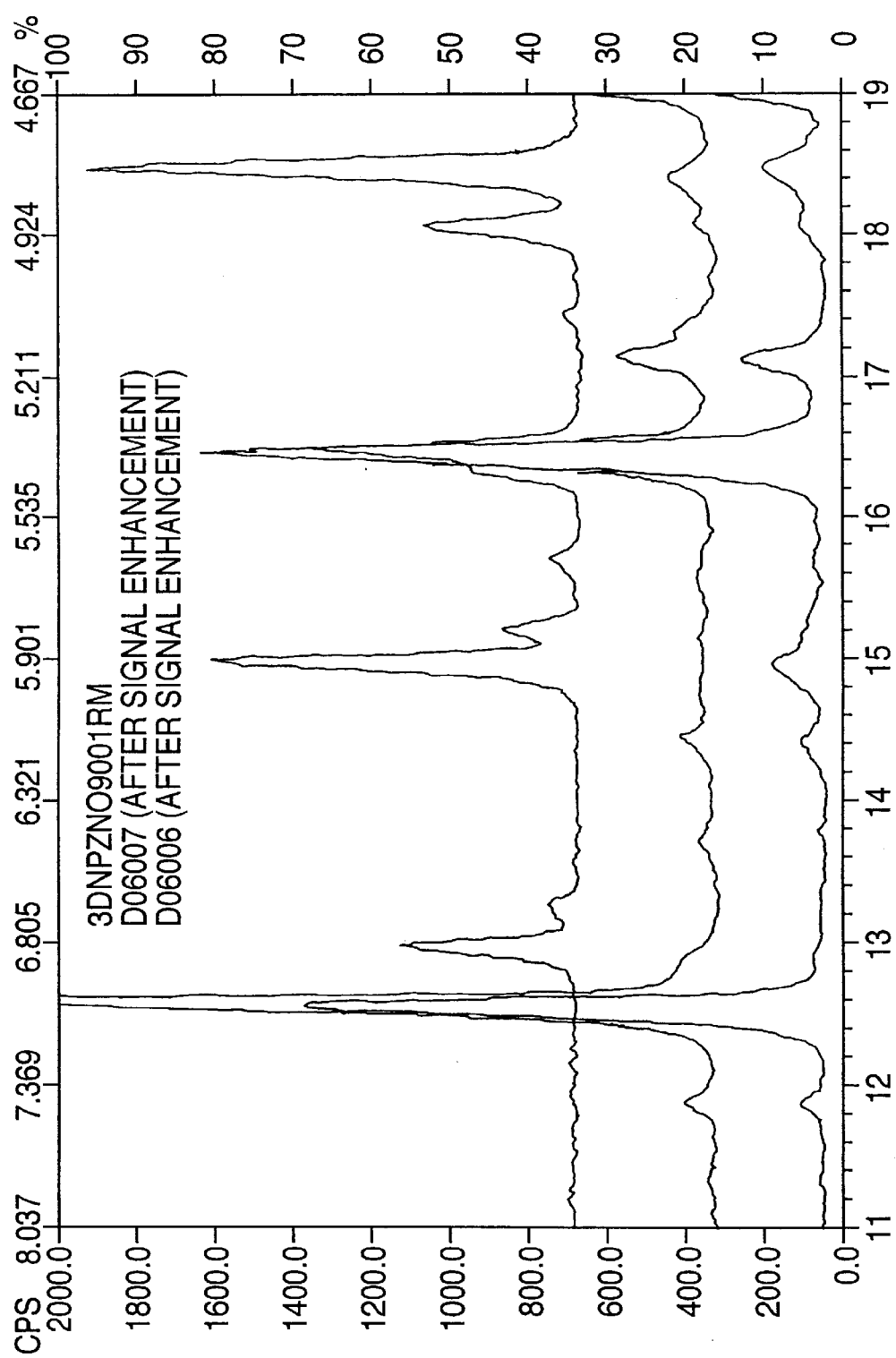
FIG. 3 is the X-ray diffraction pattern of (top to bottom) donepezil hydrochloride with crystalline form I, donepezil hydrochloride tablets prepared by wet granulation, (30 mg) after signal enhancement and donepezil hydrochloride tablets prepared by dry granulation (30 mg) after signal enhancement.

Of special interest is the area around $2\theta=15°$. At this region there is a strong absorption of crystalline donepezil hydrochloride, whereas this region is free of placebo absorption. Aricept® tablets and tablets prepared by dry granulation (that retains the crystalline form of the donepezil hydrochloride used) show clearly a peak at $2\theta=15°$. This peak is totally absent at the tablets prepared by wet granulation. Moreover, the X-ray diffraction patterns of the tablets prepared by wet granulation and the placebo are similar. The absence of extra absorption peaks in the tablet pattern indicates that there is no contribution from the donepezil hydrochloride in the tablet, showing it being amorphous (lack of crystallinity).

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Tablets were prepared by conventional dry granulation containing the following:

| Ingredient | Amount (mg) |
| --- | --- |
| Donepezil hydrochloride | 10.0 |
| Lactose monohydrate | 168.0 |
| Microcrystalline cellulose | 64.1 |
| Maize starch | 28.0 |
| Hydroxypropylcellulose | 8.4 |
| Magnesium stearate | 1.5 |

The tablets thus obtained were coated in a conventional manner with

| Ingredient | Amount (mg) |
| --- | --- |
| Opadry Y-1-7000 | 8.0 |
| Yellow iron oxide | 0.012 |
| Total weight of tablet | 288.0 |

EXAMPLE 2

Tablets of donepezil hydrochloride having the same composition as in example 1 were prepared by wet granulation. Donepezil hydrochloride was dissolved in water and the solution was mixed with a mixture of lactose monohydrate, microcrystalline cellulose, maize starch and hydroxypropylcellulose. The mixture was dried and sieved. Magnesium stearate was added with mixing and the granulate was compressed according to specifications. The tablets were coated as described in example 1.

EXAMPLE 3

A 10% aqueous solution of donepezil hydrochloride in was lyophilized. The material obtained was kept at 40° C. and 75% relative humidity. Samples were tested periodically by HPLC to determine the formation of degradation products.

| Time (months) | Impurities |
| --- | --- |
| 0 | Largest 0.1%; total 0.4% |
| 3 | Largest 0.1%; total 0.4% |
| 6 | Largest 0.1%; total 0.4% |

It will be evident to those skilled in the art that the invention is not limited to details of the foregoing illustrative examples and that the present invention may be embodied in other specific forms without departing from the essential attributes thereof, and it is therefore desired that the present embodiments examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A stable pharmaceutical composition for the treatment of dementia or Alzheimer's disease in which the active therapeutical agent is donepezil hydrochloride in an amorphous state.

2. A pharmaceutical composition according to claim 1 that is a tablet.

3. A pharmaceutical composition according to claim 1 in which the amount of donepezil hydrochloride amorphous is between 1 to 30 mg.

4. Stable donepezil hydrochloride amorphous.

* * * * *